United States Patent [19]

Molinari

[11] Patent Number: 5,037,432
[45] Date of Patent: Aug. 6, 1991

[54] ADJUSTABLE APPARATUS FOR REMOVING SURFACE PORTIONS OF HUMAN TISSUE

[75] Inventor: Lorenzo Molinari, Via Servais, 56, 10146 Torino, Italy

[73] Assignees: Lorenzo Molinari; Otello Ginebri, both of Turin, Italy

[21] Appl. No.: 277,331

[22] Filed: Nov. 28, 1988

[30] Foreign Application Priority Data

Nov. 27, 1987 [IT] Italy .............................. 53845/87[U]

[51] Int. Cl.$^5$ ............................................. A61B 17/32
[52] U.S. Cl. ...................................... 606/131; 51/424; 606/167; 604/35
[58] Field of Search ............... 604/289, 290, 293, 294, 604/313, 315, 35; 606/131, 132, 159, 169; 51/424, 439; 433/88

[56] References Cited

U.S. PATENT DOCUMENTS

| | | | |
|---|---|---|---|
| 2,608,032 | 8/1952 | Garver | 51/439 |
| 2,921,585 | 1/1960 | Schumann | 606/131 |
| 3,085,573 | 4/1963 | Meyer . | |
| 3,574,239 | 4/1971 | Sollerud | 604/289 |
| 3,715,838 | 2/1973 | Young et al. | 51/424 |
| 4,560,373 | 12/1985 | Sugino et al. . | |
| 4,646,480 | 3/1987 | Williams | 51/424 |
| 4,676,749 | 6/1987 | Mabille | 51/439 |
| 4,757,814 | 7/1988 | Wang et al. . | |

FOREIGN PATENT DOCUMENTS

| | | |
|---|---|---|
| 0258901 | 9/1988 | European Pat. Off. . |
| 3421390 | 12/1985 | Fed. Rep. of Germany . |
| 234608 | 4/1986 | German Democratic Rep. . |
| 553076 | 12/1956 | Italy ..................................... 51/424 |
| 1184922 | 10/1987 | Italy . |

Primary Examiner—Stephen C. Pellegrino
Assistant Examiner—Ralph A. Lewis
Attorney, Agent, or Firm—Kane Dalsimer Sullivan Kurucz Levy Eisele and Richard

[57] ABSTRACT

The apparatus is usable to remove surface portions of human tissue in an adjustable manner and essentially comprises a tool provided with a supply tube along which abrasive reducing substances are conveyed under pressure. A throughhole in the head disposed along the axis of the tube permits the substances to abrade the region of tissue facing the hole. A collection tube in which is created a depression is provided for the purpose of removing under suction both the reducing substances and the portions of tissue removed during the treatment.

12 Claims, 2 Drawing Sheets

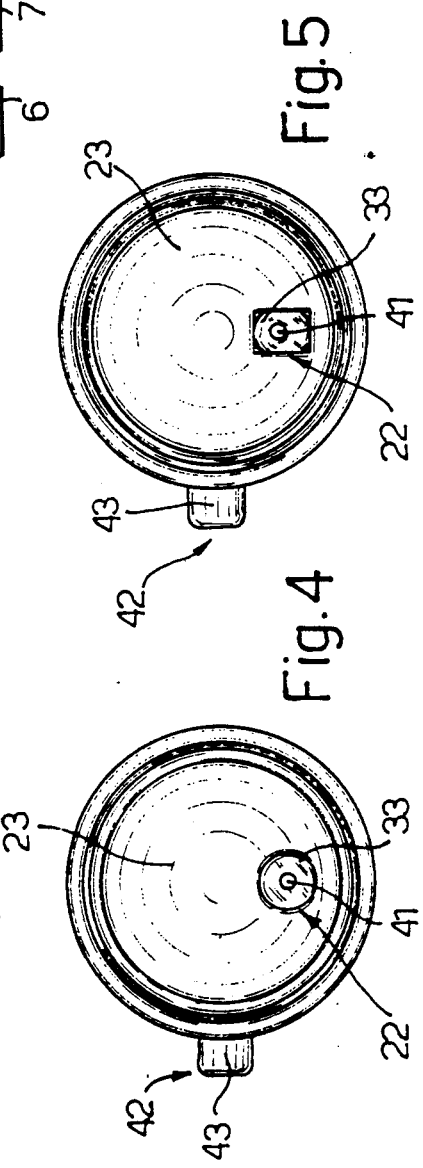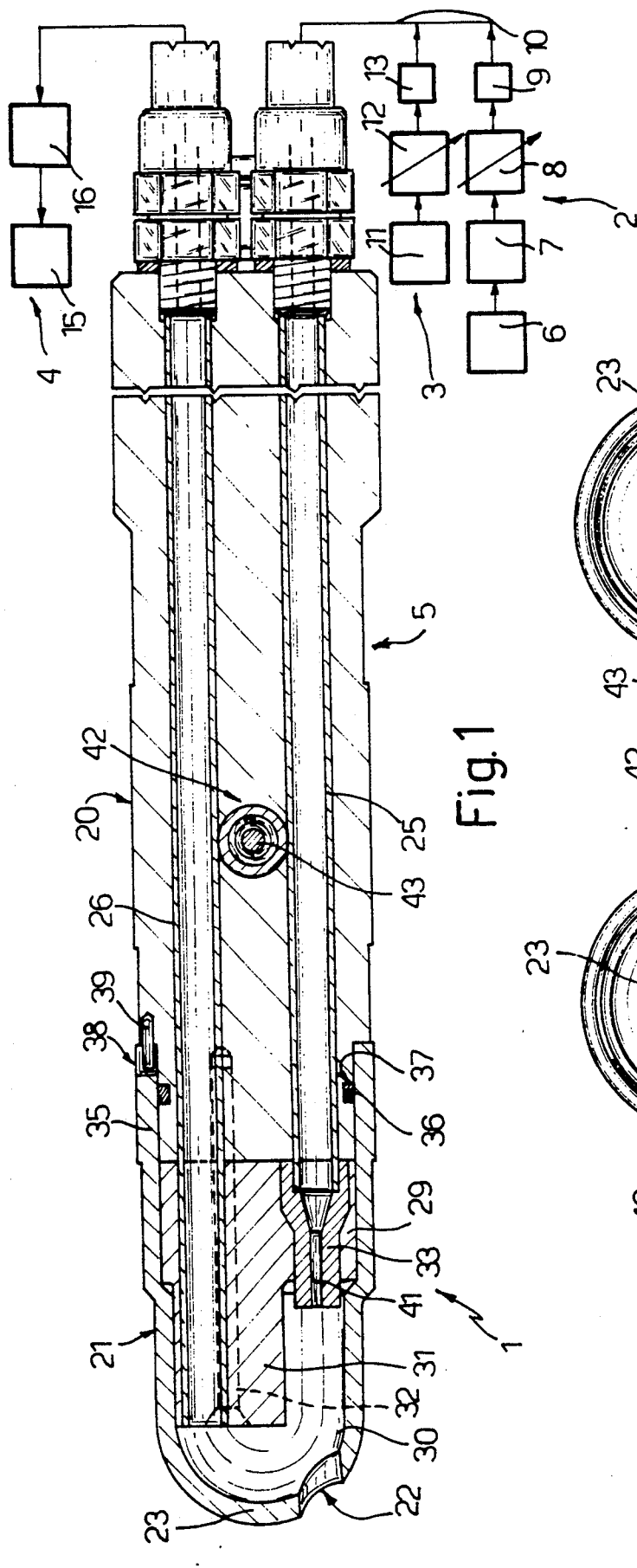

ADJUSTABLE APPARATUS FOR REMOVING SURFACE PORTIONS OF HUMAN TISSUE

BACKGROUND OF THE INVENTION

The present invention relates to an apparatus for controlled removal of surface portions of human tissue.

More particularly, the present invention relates to an apparatus able to effect a controlled application of reducing substances onto human tissue, for example the skin, for the purpose of obtaining a superficial abrasion of adjustable magnitude. For example, this abrasion could be of minimum value (known in general as "peeling" and consisting essentially in a removal of the outermost layers of the epidermis), or else of maximum value and consisting in a deep abrasion which could also involve the dermis.

SUMMARY OF THE INVENTION

The object of the present invention is to provide for the removal of surface layers of human tissue in an adjustable manner, which will be easy to use and which does not require for its construction the use of high technology components.

The object is achieved with the present invention as it relates to an apparatus for removing surface portions of human tissue, characterized by the fact that it comprises:
- pressurized fluid generating means;
- reducing substance supply means;
- suction means; and
- a tool having a supply tube with an inlet connected to the said pressure fluid generating means and the said reducing substance generating means, a throughhole in a head disposed along the axis of the said supply tube in a position facing an outlet from the tube itself to permit the said reducing substances to strike, in use, the said tissue removing the said surface portions, and a collection tube connected to the said suction means for the purpose of sucking both the said reducing substances and the said removed portions of surface tissue, both being stationary, in use, on the surface of the said tissue.

BRIEF DESCRIPTION OF THE DRAWINGS

For a better understanding of the present invention a preferred embodiment is described hereinafter purely by way of non-limitative example and with reference to the attached drawings, in which:

FIG. 1 is a schematic partially sectioned view of an apparatus formed according to the present invention;

FIG. 4 is a side view from the left of the above-mentioned detail of FIG. 1; and FIG. 5 is a side view from the left of an equivalent form to the detail of FIG. 4.

DETAILED DESCRIPTION OF THE INVENTION

Figure 3:
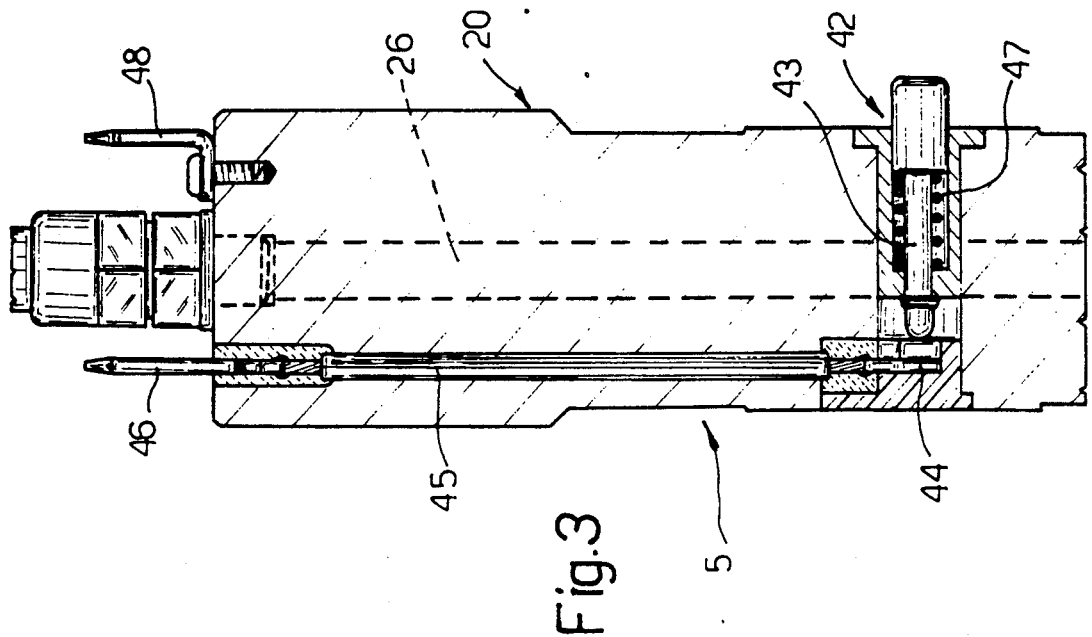
FIG. 3 is a section taken on the line III—III of FIG. 2.
Figure 2:
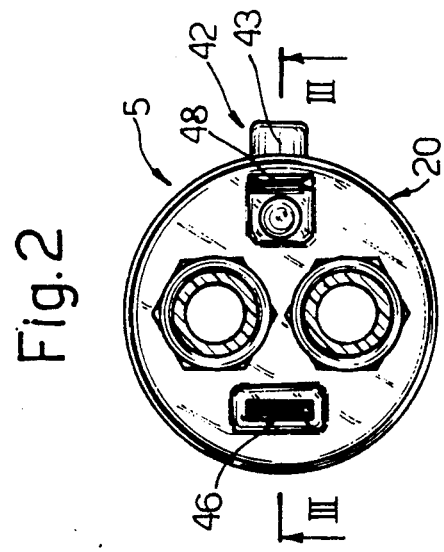
FIG. 2 is a side view from the right of a detail of FIG. 1.

With particular reference to FIG. 1, an apparatus for controlled removal of portions of human tissue by the controlled application of reducing substances is generally indicated with the reference numeral 1.

The pre-eminent utilization of the apparatus 1 is envisaged for effecting abrasions of different extent and depth of portions of human skin.

Purely by way of non-limitative example, the apparatus 1 could be utilized for removing portions of human tissue in such a way as to obtain aesthetic improvements in the following cases: hypotrophic or hypertrophic sunken scars consequent on surgical operations or recent or old burns, or of various nature both recent and of old date (for example scarring resulting from acne); cheloids; hyperpigmentated cutaneous dyschromia; senile lentigo, gravidic or oestroprogestinic chloasma, post inflammatory melanodermy or melandoermy from photo sensitising agents, etc; small surface roughnesses on the face; tears both of the "striae cutis rubrae" type and of the pearly type etc.

The apparatus 1 essentially comprises:
- pressurized fluid generator means 2, conveniently generating compressed air;
- abrasive or reducing substance supply means 3, supplying, for example, microcrystals of quartz, metal, dust or derivatives of aluminium (for example corundum), possibly having different grain size diameters;
- suction means 4; and
- a tool 5 constituting the instrument manipulated by the medical operator to remove the said portions of tissue.

The pressurized fluid generator means 2 is essentially constituted by a compressor 6 which maintains under pressure air contained within a reservoir 7, a pressure regulator 8 connected in series with an output from the reservoir 7, and a solenoid valve 9 which allows the air under pressure to flow out along the duct 10.

The supply means 3 comprise a reservoir 11 connected to the duct 10 by means of a flow regulator 12 and a solenoid valve 13.

The suction means 4 is essentially constituted by a suction pump 15 and a collection reservoir 16 connected to it.

The tool 5 has a substantially cylindrical structure and is constituted by a cylindrical body 20 surmounted by a coaxial bell-like element 21 having a bottom wall 23 delimited by a pair of spherical surfaces. A portion of the bottom wall 23, inclined with respect to the longitudinal axis of the bell-like element 21, is provided with a throughhole 22, which is thus disposed offset from the axis of the element 21 with a throughhole 22 disposed off-set from the axis in a bottom wall 23 of the element 21 delimited by a pair of spherical surfaces. In use, this wall 23 is laid over the surface of the tissue to be subjected to treatment in such a way that the hole 22 faces the specific region in which the said tissue portions must be removed. Through this hole 22 the said reducing substances transit under the thrust of the compressed air provided by the pressurized fluid generator means 2, causing removal of the portions of tissue in the amount desired by the operator.

The cylindrical body 20, conveniently made of electrically conductive material, houses two longitudinal parallel tubes 25, 26 which have respective first ends connected to the duct 10 and the suction pump 15 respectively, and respective second ends, opposite the first ends, which open into a chamber 30 essentially delimited by the bell-like element 21, by a block 31 fixed to the body 20 by means of a screw 32 and supporting the second end of the tube 26, and by a nozzle 33 maintained in position around the second end of the tube 26 by the block 31.

It is seen in particular that the block 31 has a substantially cylindrical structure and a first end surface which engages a head surface of the body 20 and an opposite base surface defining, with the respective surface of the bottom wall 23 of the element 21, a portion of the chamber 30 in the form of a spherical cap. Moreover, it is seen that the block 31 has a recessed portion 29 housing the said nozzle 33. In this way the distance between the nozzle 33 and the hole 22 is greater than the distance between this latter and the tube 26, and this makes the suction action exerted by the pump 15 particularly effective.

Given the notable abrasion which the said reducing substances can exert on the internal surfaces of the element 21 and the tubes 25, 26 and on the nozzle 33, particularly strong materials have been used for the production of these components, for example tungsten steel for the element 21, special steel for the tubes 25, 26 and cemented carbides, for example tungsten carbide and others, known as "WIDIA" (registered trade mark) for the nozzle 33.

The rim of the side wall 35 of the bell 21 establishes a sealed coupling with a corresponding facing surface of the body 20 by means of an elastic ring 36 housed within an annular groove 37 in the body 20. Further, the element 21 establishes with this body 20 an predetermined angular coupling by reason of its seat 38 which engages a respective peg 39 extending peripherally in the longitudinal direction of the body 20. The reason for this is to maintain the throughhole 22 and a duct 41 of the nozzle 33 on the same axis for the purpose of permitting the reducing substances to strike, in use, therethrough with an inclined incident angle, and therefore with greater effectiveness against the surfaces of the tissue subjected to treatment.

With particular reference to FIG. 3, it is seen that the cylindrical body 20 supports an electric switch 42, essentially constituted by a conductive pin 43 and a conductive plate 44 connected, by means of a cable 45, to an electrical connector 46 fixed at the end of the body 20 on the end opposite that supporting the bell-shape element 21. In particular, the pin 43 is mounted transversely with respect to the body 20 and is movable, against the action exerted by a coil spring 47, between a rest position in which electrical contact with the plate 44 is not established and a working position in which such electrical contact is established. It is further observed that the body 20 has a further electrical connector 48 fixed thereto defining, with the connector 46 mentioned above, the terminals of the push button 42, the function of which is that of causing, in a manner not illustrated, the solenoid valves 9 and 13 and the suction pump 15 to be enabled.

Finally with particular reference to FIG. 4, it is seen that the throughhole 22 has in plan a circular section. In another possible equivalent embodiment adapted for example, to particular working conditions, this hole could have a rectangular section (FIG. 5). In use, the reducing substances, in the required quantity adjusted by means of the flow regulator 12, are conveyed by the air under pressure, also predetermined by means of the pressure regulator 8, from the duct 10 to the throughhole 22 by the tube 25, the nozzle 33 and the chamber 30.

The delivery of the reducing substances takes place under the control of the operator who preliminarily positions the tool 5 in such a way that the throughhole 22 faces the region to be subjected to treatment, after which he presses the pushbutton 42 to cause excitation of the solenoid valves 9 and 13 and supply to the suction pump 15.

These substances strike the region of tissue facing the hole 22 causing an amount of abrasion desired by the operator and consequently removing surface portions of this tissue. Subsequently the abrasive substances and the portions of tissue removed which lie over the above-mentioned zone are sucked by the pump 15 through the tube 26 and conveyed to the interior of the reservoir 16.

The apparatus formed according to the present invention has numerous advantages.

First of all, and of fundamental importance, is the possibility of adjusting the pressure of the air and the quantity of reducing substances utilised, being able in this way to obtain an abrasion of the tissue by a desired amount.

Alignment of the exit duct of the reducing substances with the hole 22 makes the action of these substances particularly effective, while the suction exerted by the pump 15 is likewise efficient because of the positioning of the end of the tube 26 close proximity to the hole 22. The reducing substances are therefore almost entirely recovered thus avoiding any unwanted dispersion.

Replacement of the element 21 in the case of the necessity of utilising a hole 22 of different shape or size from that mounted on the tool 5 is particularly simple and immediate.

Control of the functioning operation of the apparatus 1 by the pushbutton 42 supported directly on the tool 5 makes the apparatus particularly manageable.

The particular shape and hemisphere of the head portion of the element 21 facilitates positioning of the hole 22 even over zones which are difficult to gain access to (wrinkles at the root of the nose etc) allowing the apparatus to be used over a wide range of use.

It is further seen that the treatment which the apparatus is able to perform is gentle and produces a massage of the treated zone, likewise encouraging the circulation of blood and the lymphatic circulation, essential for the reconstruction of the cutaneous tissue.

Finally, it is clear that the apparatus 1 described above can have modifications and variations introduced thereto without departing from the present invention.

I claim:

1. A hand tool for removing surface portions of human tissue by superficial abrasion caused by a stream of a mixture of air with at least one granular abrasive substance striking on the surface of the tissue to be removed, said tool comprising an elongated manipulative body (20), a supply tube (25, 33) for said mixture, a collection tube (26, 31) for the purpose of sucking-in both said mixture and the removed portions of said tissue, each one of said tubes (25, 33; 26, 31) having a terminal portion (33, 31) with a free end, and an operating head (21) secured to said manipulative body (20) at the distal end thereof and housing said terminal portions (33, 31), said body (20) housing the other portion (25, 26) of said tubes (25, 33; 26, 31), said head (21) having a longitudinal axis and being provided with a wall (23) having a wall portion inclined and offset with respect to the said axis, a throughhole (22) being provided in said wall portion and internally communicating with said free ends of said terminal portions (33, 31), said throughhole (22) being aligned with said terminal portion (33) of said supply tube (25, 33) so that, by keeping in contact said throughhole (22) with said surface, said stream of mixture travelling through the terminal portion (33) of said supply tube (25, 33) and throughhole (22) is caused to strike said surface with an inclined incident angle.

2. A hand tool according to claim 1, wherein the terminal portion of said supply tube (25, 33) includes a nozzle (33) adapted to convey said mixture toward said throughhole (22).

3. A hand tool according to claim 2, wherein the distance between the free end of said nozzle (33) and said throughhole (22) is greater than the distance between said throughhole (22) and the free end of the terminal portion (31) of said collection tube (26, 31).

4. A hand tool according to claim 2 wherein said nozzle is made of a material particularly resistant to abrasion by the abrasive substances.

5. A hand tool according to claim 4, wherein the material of which said nozzle is formed is a compound of cemented carbides with a predominance of tungsten carbides.

6. A hand tool according to claim 1, wherein said tubes (25, 33; 26, 31) are parallel to each other, and wherein said body (20) has an essentially cylindrical shape said head being formed of a bell-shaped element (21) coaxial with and closing said body (20) and carrying said throughhole (22).

7. A hand tool according to claim 6, wherein said bell-shape body (21) establishes with said body (20) a predetermined angular coupling and fluid-tight seal.

8. A hand tool according the claim 7, wherein between said body (20) and said bell-shape element (21) there is interposed a resilient sealing ring (36).

9. A hand tool according to claim 7, wherein said body (20) and said bell-shape element (21) have respective coupling means (39, 38) cooperatible with one another to establish said predetermined angular coupling.

10. Apparatus for removing surface portions of human tissue by superficial abrasion caused by a stream of a mixture of pressurized air with at least one granular abrasive substance striking on the surface of the tissue to be removed, comprising a hand tool (5) to be applied to said surface, first supply means (2) for supplying said pressurized air, second supply means (3) for supplying said abrasive substance, suction means (4), said tool (5) comprising an elongated manipulative body (20), a supply tube (25, 33) for conveying said mixture, duct means for conveying said mixture from said first and second supply means, a collection tube (26, 31) for the purpose of sucking-in both said mixture and the removed portions of said tissue, each one of said tubes (25, 33; 26, 31) having a terminal portion (33, 31) with a free end, the other portion end of said supply tube (25, 33) being connected to said duct means and the other end of said collection tube (26, 31) being connected to said suction means (4), and an operating head (21) secured to said manipulative body (20) at the distal and thereof and housing said terminal portions (33, 31), said body (20) housing the other portion (25, 26) of said tubes (25, 33; 26, 31), said head (21) having a longitudinal axis and being provided with a wall (23) having a wall portion inclined and offset with respect to said axis, a throughhole (22) provided in said wall portion and internally communicating with the free ends of said terminal portions (33, 31), said throughhole (22) being aligned with the terminal portion (33) of said supply tube (25, 33) so that, by keeping in contact said throughhole (22) with said surface, said stream of mixture travelling through the terminal portion (33) of said supply tube (25, 33) and said throughhole (22) is caused to strike said surface with an inclined incident axis.

11. Apparatus according to claim 10, further including said abrasive substance, wherein said abrasive substance is preferably constituted by aluminum derivatives such as corundum.

12. Apparatus according to claim 10, wherein said first supply means (2) includes a pressurized air generator means (6) and said suction means (4) includes a suction pump (15) and a collection reservoir (16) connected thereto for collecting said removed portions of tissue, wherein said apparatus further comprises electrical means for operating said generator means and said suction pump.

* * * * *